United States Patent
Karan et al.

(10) Patent No.: US 12,023,330 B2
(45) Date of Patent: Jul. 2, 2024

(54) USE OF MANZAMINES AS ANTIPROLIFERATIVE AGENT

(71) Applicants: University of South Carolina, Columbia, SC (US); MUSC Foundation for Research Development, Charleston, SC (US)

(72) Inventors: Dev Karan, Muskego, WI (US); Mark T. Hamann, Mount Pleasant, SC (US)

(73) Assignee: UNIVERSITY OF SOUTH CAROLINA and MU

( * ) Notice: Subject to any disclaimer, the term of this patent is extended or adjusted under 35 U.S.C. 154(b) by 366 days.

(21) Appl. No.: 17/168,319

(22) Filed: Feb. 5, 2021

(65) Prior Publication Data

US 2021/0244725 A1   Aug. 12, 2021

Related U.S. Application Data

(60) Provisional application No. 62/970,750, filed on Feb. 6, 2020.

(51) Int. Cl.
*A61K 31/475* (2006.01)
*A61P 35/00* (2006.01)

(52) U.S. Cl.
CPC ............ *A61K 31/475* (2013.01); *A61P 35/00* (2018.01)

(58) Field of Classification Search
CPC .................................................... A61K 31/475
See application file for complete search history.

(56) References Cited

PUBLICATIONS

Lin et al., Mar. Drugs 2018, 16,252.*
Richter et al. Bioorganic & Medicinal Chemistry (2019), 27(23), 115145.*
Ko et al. , Scientific Reports (2019), 9(1), 1-12.*
McMahon et al. (2000) Pinedo et al. (2000).*

* cited by examiner

*Primary Examiner* — Paul V Ward

(57) ABSTRACT

Described herein are methods and systems for using an alkaloid, such as manzamine A, for anti-proliferative effects at relatively low and non-cytotoxic concentrations (up to 4 µM) wherein manzamine A blocks cell cycle progression in cervical cancer cell lines and regulates cell cycle-related genes, including restoration of p21 and p53 expression inducing apoptosis.

6 Claims, 8 Drawing Sheets

Specification includes a Sequence Listing.

USE OF MANZAMINES AS ANTIPROLIFERATIVE AGENT

TECHNICAL FIELD

The subject matter disclosed herein is generally directed to methods and systems for using an alkaloid, such as Manzamine A, for anti-proliferative effects at relatively low and non-cytotoxic concentrations (up to 4 µM) wherein Manzamine blocks cell cycle progression in cervical cancer cell lines and regulates cell cycle-related genes, including restoration of p21 and p53 expression inducing apoptosis.

BACKGROUND

Natural products remain an important source of drug leads covering unique chemical space and providing significant therapeutic value for the control of cancer and infectious diseases resistant to current drugs. Natural products have a long history of use in the treatment of various diseases including cancer. The primary sources of successful natural product cancer therapeutics have been from microbes and plants from the environment. In fact, more than 49% of currently used anti-cancer agents are either natural products or directly derived from natural products.

Marine natural products from animals, plants, and bacteria continue to provide a highly productive resource for the discovery and development of new, innovative disease treatments with novel mechanisms of action. The marine environment is unique with regard to the high degree of competition among species, and the kinetics of metabolite transport in densely populated aqueous environments make marine organisms a rich source of structurally-diverse and complex, bioactive natural products. Sessile marine organisms such as sponges are particularly rich in this regard, as they depend solely on either physical or chemical mechanisms to escape predation. Marine-derived bioactive terpenes, alkaloids, macrolides and other compounds isolated from aquatic fungi, cyanobacteria, algae, sponges, and tunicates, have all been found to exhibit various anti-cancer activities.

The present disclosure has discovered the anti-cancer activity of a natural product manzamine A from an Indo-Pacific sponge following various in vitro cellular assays targeting cervical cancer (C33A, HeLa, SiHa, and CaSki). Accordingly, it is an object of the present disclosure to provide methods and systems for its use as a treatment for cancer.

Citation or identification of any document in this application is not an admission that such a document is available as prior art to the present disclosure.

SUMMARY

The above objectives are accomplished according to the present disclosure by providing a method for suppressing proliferation of cancer cells. The method includes administering a therapeutically effective amount of at least one alkaloid, wherein the alkaloid binds with at least one kinase involved with oncogenesis, and wherein the bound alkaloid and kinase regulate at least one oncoprotein associated with a cancer. Further, the alkaloid may be a manzamine analog. Again, the manzamine analog may be manzamine A. Still yet, the kinase may be Casein Kinase 2. Again, the oncoprotein has a protein sequence of SEQ. 1. Still yet, the alkaloid may be noncytotoxic in concentrations up to 4 µM. Further, the cancer may include cervical, colon, pancreatic, prostrate, and breast cancer. Yet further, the alkaloid may be naturally occurring. Yet still, administering the alkaloid may restore expression of proteins inducing cell apoptosis. Still again, the at least one alkaloid may be administered in a dose concentration ranging from 1 µM to 4 µM.

In a further embodiment, a system is provided for suppressing proliferation of cancer cells. The system may include administering a pharmaceutically acceptable carrier containing an affective amount of at least one an alkaloid, the alkaloid may bind with at least one kinase involved with oncogenesis, and the bound alkaloid and kinase regulate at least one oncoprotein associated with a cancer. Further, the alkaloid may be a manzamine analog. Still further, the manzamine analog may be manzamine A. Yet again, the kinase may be Casein Kinase 2. Still yet, the oncoprotein may have a protein sequence of SEQ. 1. Again, the alkaloid may be noncytotoxic in concentrations up to 4 µM. Further again, the cancer may include cervical, prostrate, colon, prostrate, and breast cancer. Still yet, the alkaloid may be naturally occurring. Again, administering the alkaloid may restore expression of proteins inducing cell apoptosis. Still further, the at least one alkaloid can be administered in a dose concentration ranging from 1 µM to 4 µM.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present disclosure will be obtained by reference to the following detailed description that sets forth illustrative embodiments, in which the principles of the disclosure may be utilized, and the accompanying drawings of which.

Figure 1:
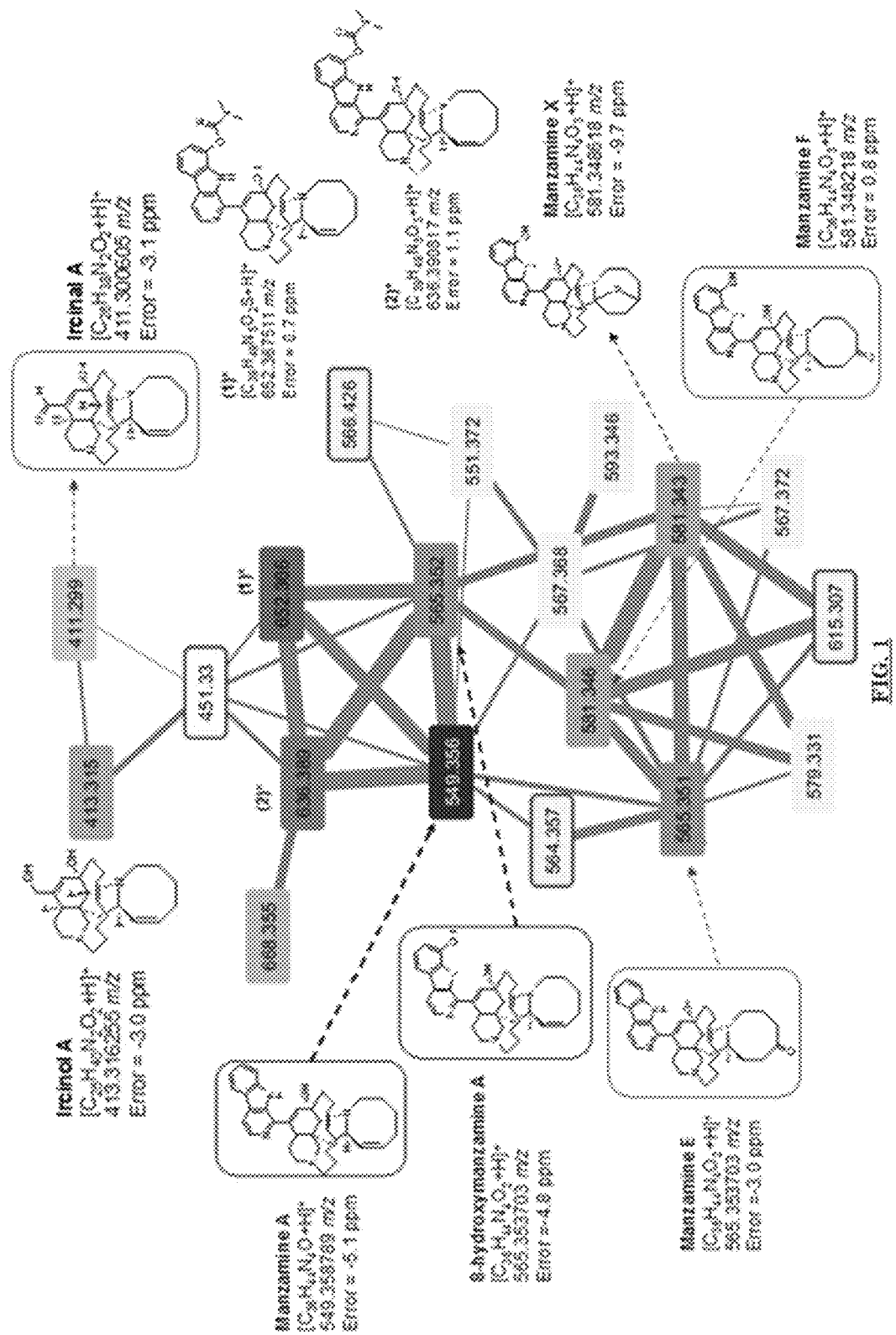
FIG. 1 shows MoIN analysis of sponge-derived alkaloids.

The figures herein are for illustrative purposes only and are not necessarily drawn to scale.

DETAILED DESCRIPTION OF THE EXAMPLE EMBODIMENTS

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further embodiment includes from the one particular value and/or to the other particular value. The recitation of numerical ranges by endpoints includes all numbers and fractions subsumed within the respective ranges, as well as the recited endpoints. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4$^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2$^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

As used herein, "about," "approximately," "substantially," and the like, when used in connection with a measurable variable such as a parameter, an amount, a temporal duration, and the like, are meant to encompass variations of and from the specified value including those within experimental error (which can be determined by e.g. given data set, art accepted standard, and/or with e.g. a given confidence interval (e.g. 90%, 95%, or more confidence interval from the mean), such as variations of +/−10% or less, +/−5% or less, +/−1% or less, and +/−0.1% or less of and from the specified value, insofar such variations are appropriate to perform in the disclosure. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, a "biological sample" may contain whole cells and/or live cells and/or cell debris. The biological sample may contain (or be derived from) a "bodily fluid". The present disclosure encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, and cell cultures from bodily fluids. Bodily fluids may be obtained from a mammal organism, for example by puncture, or other collecting or sampling procedures.

As used herein, "agent" refers to any substance, compound, molecule, and the like, which can be administered to a subject on a subject to which it is administered to. An agent can be inert. An agent can be an active agent. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

As used herein, "active agent" or "active ingredient" refers to a substance, compound, or molecule, which is biologically active or otherwise that induces a biological or physiological effect on a subject to which it is administered to. In other words, "active agent" or "active ingredient" refers to a component or components of a composition to which the whole or part of the effect of the composition is attributed.

As used herein, "administering" refers to any suitable administration for the agent(s) being delivered and/or subject receiving said agent(s) and can be oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition to the perivascular space and adventitia. For example, a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration routes can be, for instance, auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes, which typically depends on the disease to be treated, subject being treated, and/or agent(s) being administered.

As used herein "cancer" can refer to one or more types of cancer including, but not limited to, acute lymphoblastic leukemia, acute myeloid leukemia, adrenocortical carcinoma, Kaposi Sarcoma, AIDS-related lymphoma, primary central nervous system (CNS) lymphoma, anal cancer, appendix cancer, astrocytomas, atypical teratoid/Rhabdoid tumors, basa cell carcinoma of the skin, bile duct cancer, bladder cancer, bone cancer (including but not limited to Ewing Sarcoma, osteosarcomas, and malignant fibrous histiocytoma), brain tumors, breast cancer, bronchial tumors, Burkitt lymphoma, carcinoid tumor, cardiac tumors, germ cell tumors, embryonal tumors, cervical cancer, cholangiocarcinoma, chordoma, chronic lymphocytic leukemia, chronic myelogenous leukemia, chronic myeloproliferative neoplasms, colorectal cancer, craniopharyngioma, cutaneous T-Cell lymphoma, ductal carcinoma in situ, endometrial cancer, ependymoma, esophageal cancer, esthesioneuroblastoma, extracranial germ cell tumor, extragonadal germ cell tumor, eye cancer (including, but not limited to, intraocular melanoma and retinoblastoma), fallopian tube cancer, gallbladder cancer, gastric cancer, gastrointestinal carcinoid tumor, gastrointestinal stromal tumors, central nervous system germ cell tumors, extracranial germ cell tumors, extragonadal germ cell tumors, ovarian germ cell tumors, testicular cancer, gestational trophoblastic disease, Hairy cell leukemia, head and neck cancers, hepatocellular (liver) cancer, Langerhans cell histiocytosis, Hodgkin lymphoma, hypopharyngeal cancer, islet cell tumors, pancreatic neuroendocrine tumors, kidney (renal cell) cancer, laryngeal cancer, leukemia, lip cancer, oral cancer, lung cancer (non-small cell and small cell), lymphoma, melanoma, Merkel cell carcinoma, mesothelioma, metastatic squamous cell neck cancer, midline tract carcinoma with and without NUT gene changes, multiple endocrine neoplasia syndromes, multiple myeloma, plasma cell neoplasms, mycosis fungoides, myelodyspastic syndromes, myelodysplastic/myeloproliferative neoplasms, chronic myelogenous leukemia, nasal cancer, sinus cancer, non-Hodgkin lymphoma, pancreatic cancer, paraganglioma, paranasal sinus cancer, parathyroid cancer, penile cancer, pharyngeal cancer, pheochromocytoma, pituitary cancer, peritoneal cancer, prostate cancer, rectal cancer, Rhabdomyosarcoma, salivary gland cancer, uterine sarcoma, Sézary syndrome, skin cancer, small intestine cancer, large intestine cancer (colon cancer), soft tissue sarcoma, T-cell lymphoma, throat cancer, oropharyngeal cancer, nasopharyngeal cancer, hypopharyngeal cancer, thymoma, thymic carcinoma, thyroid cancer, transitional cell cancer of the renal pelvis and ureter, urethral cancer, uterine cancer, vaginal cancer, cervical cancer, vascular tumors and cancer, vulvar cancer, and Wilms Tumor.

As used herein, "chemotherapeutic agent" or "chemotherapeutic" refers to a therapeutic agent utilized to prevent or treat cancer.

As used herein, "control" can refer to an alternative subject or sample used in an experiment for comparison purpose and included to minimize or distinguish the effect of variables other than an independent variable.

The term "optional" or "optionally" means that the subsequent described event, circumstance or substituent may or may not occur, and that the description includes instances where the event or circumstance occurs and instances where it does not.

As used herein, "dose," "unit dose," or "dosage" can refer to physically discrete units suitable for use in a subject, each unit containing a predetermined quantity of a naturally occurring alkaloid, such as manzamine A, and/or a pharmaceutical formulation thereof calculated to produce the desired response or responses in association with its administration.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "polymer" refers to molecules made up of monomers repeat units linked together. "Polymers" are understood to include, but are not limited to, homopolymers, copolymers, such as for example, block, graft, random and alternating copolymers, terpolymers, etc. and blends and modifications thereof. "A polymer" can be can be a three-dimensional network (e.g. the repeat units are linked together left and right, front and back, up and down), a two-dimensional network (e.g. the repeat units are linked together left, right, up, and down in a sheet form), or a one-dimensional network (e.g. the repeat units are linked left and right to form a chain). "Polymers" can be composed, natural monomers or synthetic monomers and combinations thereof. The polymers can be biologic (e.g. the monomers are biologically important (e.g. an amino acid), natural, or synthetic.

As used herein, the term "radiation sensitizer" refers to agents that can selectively enhance the cell killing from irradiation in a desired cell population, such as tumor cells, while exhibiting no single agent toxicity on tumor or normal cells.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed by the term "subject".

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used interchangeably herein, the terms "sufficient" and "effective," can refer to an amount (e.g. mass, volume, dosage, concentration, and/or time period) needed to achieve one or more desired and/or stated result(s). For example, a therapeutically effective amount refers to an amount needed to achieve one or more therapeutic effects.

As used herein, "tangible medium of expression" refers to a medium that is physically tangible or accessible and is not a mere abstract thought or an unrecorded spoken word. "Tangible medium of expression" includes, but is not limited to, words on a cellulosic or plastic material, or data stored in a suitable computer readable memory form. The data can be stored on a unit device, such as a flash memory or CD-ROM or on a server that can be accessed by a user via, e.g. a web interface.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as cancer and/or indirect radiation damage. The effect can be therapeutic in terms of a partial or complete cure of a disease, condition, symptom or adverse effect attributed to the disease, disorder, or condition. The term "treatment" as used herein covers any treatment of cancer and/or indirect radiation damage, in a subject, particularly a human and/or companion animal, and can include any one or more of the following: (a) preventing the disease or damage from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values the specified components in the disclosed composition or formulation are equal to 100.

As used herein, "water-soluble", generally means at least about 10 g of a substance is soluble in 1 L of water, i.e., at neutral pH, at 25° C.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present disclosure. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the disclosure. For example, in the appended claims, any of the claimed embodiments can be used in any combination.

All patents, patent applications, published applications, and publications, databases, websites and other published materials cited herein are hereby incorporated by reference to the same extent as though each individual publication, published patent document, or patent application was specifically and individually indicated as being incorporated by reference.

Kits

Any of the compounds and/or formulations described herein can be presented as a combination kit. As used herein, the terms "combination kit" or "kit of parts" refers to the compounds, compositions, formulations, particles, cells and any additional components that are used to package, sell, market, deliver, and/or administer the combination of elements or a single element, such as the active ingredient, contained therein. Such additional components include, but are not limited to, packaging, syringes, blister packages, bottles, and the like. When one or more of the compounds, compositions, formulations, particles, cells, described herein or a combination thereof (e.g., agent(s)) contained in the kit are administered simultaneously, the combination kit can contain the active agent(s) in a single formulation, such as a pharmaceutical formulation, (e.g., a tablet, liquid preparation, dehydrated preparation, etc.) or in separate formulations. When the compounds, compositions, formulations, particles, and cells described herein or a combination thereof and/or kit components are not administered simultaneously, the combination kit can contain each agent or other component in separate pharmaceutical formulations. The separate kit components can be contained in a single package or in separate packages within the kit.

In some embodiments, the combination kit also includes instructions printed on or otherwise contained in a tangible medium of expression. The instructions can provide information regarding the content of the compounds and/or formulations, safety information regarding the content of the compounds and formulations (e.g., pharmaceutical formulations), information regarding the dosages, indications for use, and/or recommended treatment regimen(s) for the compound(s) and/or pharmaceutical formulations contained therein. In some embodiments, the instructions can provide directions and protocols for administering the compounds and/or formulations described herein to a subject in need thereof. In some embodiments, the instructions can provide one or more embodiments of the methods for administration of the alkaloid and/or pharmaceutical formulation thereof such as any of the methods described in greater detail elsewhere herein.

Manzamine A demonstrated anti-proliferative effects at relatively low and non-cytotoxic concentrations up to 4 µM, including but not limited to ranges of 1 µM to 4 µM, 2 µM to 4 µM, 3 µM to 4 µM or variations of same such as 1.5 µM to 4 µM, 2.5 to 4 µM, 3.5 µM to 4 µM, etc., including intervals within these mentioned ranges. Mechanistic investigations confirmed that manzamine blocked cell cycle progression in cervical cancer cell lines and regulated cell cycle-related genes, including restoration of p21 and p53 expression inducing apoptosis. Molecular interlocking studies showed compatible binding of manzamine with Casein Kinase 2, which in turn regulates oncoprotein SIX1 associated with oncogenesis in cervical cancer. SIX1 protein is a homeodomain-containing transcription factor expressed at high levels in a variety of cancers, including cervical, colon, prostate, and breast cancers, and has been associated aggressive clinical behavior of cancers and poor outcomes. In a direct comparison to apigenin, a known inhibitor of CK2a, we demonstrated that manzamine A is about ten-times more potent in inhibiting CK2α and SIX1 proteins than apigenin. These data suggest that our approach of molecular networking facilitated the efficient identification, de-replication, and assignment of structures from the manzamine class and revealed the significant potential in design and development of novel manzamine analogs efficacious for therapeutic treatment of cancer.

Our data demonstrated the anti-proliferative effects of manzamine A at relatively low and non-cytotoxic concentrations (up to 4 µM). Mechanistic investigations confirmed that manzamine A blocked cell cycle progression in SiHa and CaSki cells at G1/S phase and regulated cell cycle-related genes, including restoration of p21 and p53 expression. In apoptotic assays, HeLa cells showed the highest sensitivity to manzamine A as compared to other cell types (C33A, SiHa, and CaSki). Interestingly, manzamine A decreased the levels of the oncoprotein SIX1 which is associated with oncogenesis in cervical cancer.

To further investigate the structure-activity relationship among manzamine A class with potential anti-cancer activity, molecular networking facilitated the efficient identification, de-replication, and assignment of structures from the manzamine class and revealed the significant potential in the design of optimized molecules for the treatment of cervical cancer. These data suggest that this sponge-derived natural product class warrants further attention about the design and development of novel manzamine analogs, which may be efficacious for preventive and therapeutic treatment of cancer. Additionally, this study reveals the significance of protecting fragile marine ecosystems from climate change-induced loss of species diversity.

Here, we studied the effect of a marine sponge product, manzamine A on cervical cancer cells. Cervical squamous dysplasia and cancer are due to infectious agents such as human papilloma virus (HPV), particularly the HPV types 16 and 18, which collectively account for an estimated 70% of all cervical cancer cases. For cervical cancer prevention, HPV vaccines (Gardasil, Gardasil 9, and Cervarix) protect against cervical infection with the HPV types included in the vaccines in women not previously exposed to HPV infection. However, HPV is a prophylactic vaccine, which must be introduced at a young age prior to HPV infection. Over 50% of women diagnosed with cervical cancer have stage II-IV disease and require combination of chemotherapy and radiation as their primary treatment. As proven clinically, these treatment modalities are associated with long-term side effects that significantly affect quality of life. Therefore, there is a continuous need to develop more effective therapies that can cure localized tumors and prevent progression and metastasis of cervical cancer.

The manzamine alkaloids are isolated from Indo-Pacific sponges and represent a group of complex β-carboline alkaloids characterized by a unique nitrogen-containing polycyclic system. While some 80 manzamine analogs have been reported over the past two decades, it is likely that many more remain to be characterized and prepared through medicinal chemistry studies. This class of alkaloids has been previously reported to possess a wide variety of biological activity, and manzamine A has emerged as a promising drug candidate for the treatment of multiple disease conditions. However, studies examining the effect of manzamine A in cancer are very limited.

In this disclosure, we demonstrate that manzamine A inhibits the growth of cervical cancer cells, inducing cell cycle arrest and stimulating apoptosis related molecular pathways. We employed molecular networking (MolN) to facilitate the design of novel analogues, that may harbor improved potential therapeutic activity against cervical cancer and other diseases. Furthermore, three novel manzamine analogues were discovered through mass spectrometry (MS) based MolN, providing new directions for the investigation of manzamine A and its mechanisms for the prevention or treatment of cervical cancer.

Molecular Networking (MolN) Facilitates Identification of Novel Manzamine A Analogues. The discovery of natural product therapeutic leads continues to be greatly facilitated by highly sensitive mass spectrometry (MS)-based analysis that allows a higher-order view of metabolic diversity present within a biological sample. Posing a considerable challenge however is the streamlining of high-content MS data for identification of new mass species with potentially therapeutic properties. Here, we employed MolN to aid in the discovery of a new manzamine alkaloids based on comparisons between MS/MS-derived data with available literature. Untargeted LC-MS/MS analysis was performed on dried total alkaloid and fractionated extracts previously prepared from the Indonesian sponge *Acanthostrongylophora* sp. The presence of manzamine constituents manzamine A (1), manzamine D (2), manzamine F (3), 8-hydroxymanzamine A (4), ircinal A (5), and ircinol A (6) were previously detected by thin-layer chromatography and NMR. See, Yousaf, M.; Hammond, N. L.; Peng, J.; Wahyuono, S.; McIntosh, K. A.; Charman, W. N.; Mayer, A. M.; Hamann, M. T. *J. Med. Chem.* 2004, 47, 3512-3517 and Rao, K. V.; Donia, M. S.; Peng, J.; Garcia-Palomero, E.; Alonso, D.; Martinez, A.; Medina, M.; Franzblau, S. G.; Tekwani, B. L.; Khan, S. I.; Wahyuono, S.; Willett, K. L.; Hamann, M. T. J. *Nat. Prod.* 2006, 69, 1034-1040. Samples were analyzed by LC-ESI-MS/MS using an Impact II qTOF (Bruker) and spectral data networked using the GNPS open-source spectral networking script, see FIG. 1 and Bandeira, N.; Tsur, D.; Frank, A.; Pevzner, P. A. *Proc. Natl. Acad. Sci.* 2007, 104, 6140-6145. FIG. 1 shows MolN analysis of sponge-derived alkaloids, with mass features color coded by mass range (yellow=400-500 m/z; blue=500-600 m/z; green=600-700 m/z; red=>700 m/z. The confirmed structure of 1, 3, 4, 5 and manzamine E were completed using 1H NMR and MS/MS. The chemical structure of 1 and 4, the most abundance metabolites were highlighted on blue boxes while 3, 5, and manzamine E on green boxes. *Two synthetic manzamine derivatives were used as control, compound 1 and compound 2, represented at the right of the figure. Putative molecular formulas were generated for all features in manzamine A network based upon high-resolution (HRMS) data (not shown) and their relationship to known major and minor manzamine constituents (manzamine A (1), $[M+H]^+$ 549.358550 m/z, $\Delta$=0.2 ppm; manzamine E, $[M+H]^+$ 565.353703 m/z, $\Delta$=0.1 ppm; manzamine F (3), $[M+H]^+$ 581.348918 m/z, $\Delta$=–0.5 ppm), as well as ircinal A (5) $[M+H]^+$ 411.300598, $\Delta$=0.0 ppm) and ircinol A (6) ($[M+H]^+$ 413.316214 m/z; $\Delta$=0.1 ppm) which served as reference mass features. Fourteen mass features were assigned that, to our knowledge, do not correspond to any known, naturally occurring manzamine A derivative that could be determined through literature or database searching.

Figure 2:
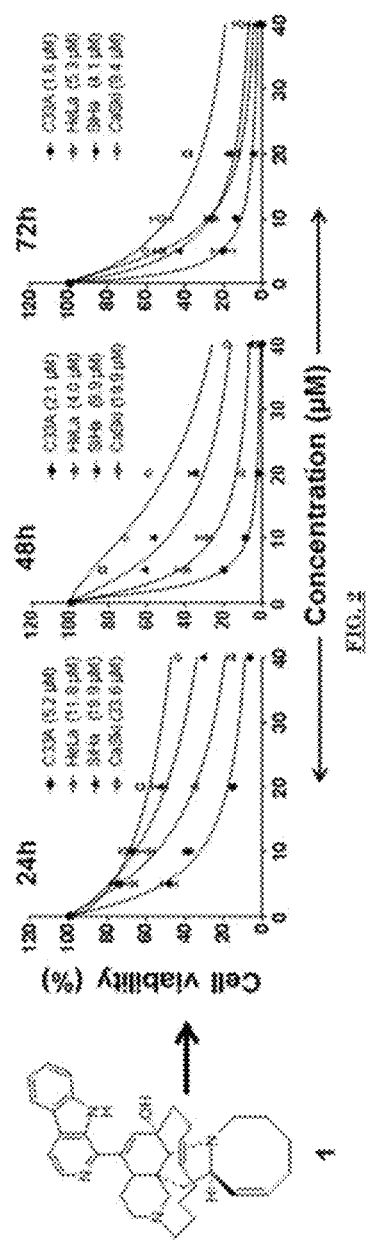
FIG. 2 shows biological effects of manzamine A on cell viability of cervical cancer cell lines (C33A, HeLa, SiHa, and CaSki).

Biological Effect of Marine Sponge Natural Product Manzamine A on Cervical Cancer Cell Growth. We determined the biological activity of manzamine A on cervical cancer cells C33A (HPV-negative), HeLa, SiHa, and CaSki (HPV16/18-positive) using a wide range of concentrations (0-40 μM) at different time points (24, 48 and 72 hours). The CellTiter-Glo cell viability assay determined the cell viability based on metabolically active cells producing ATP in the cell culture. The cell viability assay showed that C33A and HeLa cells were more sensitive to manzamine A with $IC_{50}$ values of 2.1 μM and 4.0 μM at 48 hours, and 1.6 μM and 5.3 μM at 72 hours as compared to SiHa and CaSki cells. However, the CaSki cells were least sensitive to manzamine A with $IC_{50}$ values of 19.9 μM and 9.4 μM at 48 and 72 hours respectively, see FIG. 2. FIG. 2 shows biological effects of manzamine A on cell viability of cervical cancer cell lines (C33A, HeLa, SiHa, and CaSki). Twenty thousand ($2 \times 10^4$) cells were seeded in ninety-six well plates and treated with a wide range of 1 μM to 40 μM concentration of manzamine A for three time points (24, 48 and 72 h). The experiment was repeated at least three times in quadruplicates from different cell preparations with similar results. Percent viable cells were used to calculate $IC_{50}$ values and are shown in the inset for all the cell lines at their respective timepoints. The percent viability values represent standard error from the mean (mean±SE).

To maintain the treatment uniformity across the cell lines, we selected optimal dose concentration of 1 to 4 μM, and treated C33A, HeLa, SiHa and CaSki cell lines. Cell growth kinetics study showed that manzamine A significantly inhibited cervical cancer cell proliferation in a time- and dose-dependent manner as compared to vehicle dimethyl sulfoxide (DMSO) control. This anti-proliferation cancer cell activity was further supported by the colony formation assays, where 2 and 4 μM of manzamine A inhibited the cell growth demonstrating a sustained, long-term ability of manzamine A to suppress cervical cancer cell growth.

Based on MoIN, the additional manzamine-related compounds such as manzamine D (2), manzamine F (3), 8-hydroxymanzamine A (4), and ircinal A (5) were tested for their biological activities targeting cervical cancer cell lines (SiHa and CaSki). Manzamine D (2), 3, and 5 did not reveal any effect on cervical cancer cell growth, however, compound 4 showed inhibition of both SiHa and CaSki cells. Since 1 and 4 exhibited anti-proliferation of cancer cells, we further tested the effect of these two analogues on normal human keratinocytes (HKc). We observed that the cell growth kinetics of the normal HKc treated with 8-hydroxymanzamine A (4) at 4 μM concentration was inhibited significantly (p=0.0022 at 48 h and p=0.0004 at 72 h) as compared to DMSO control. On the other hand, manzamine A (1) showed no adverse effect on normal HKc. These data suggest that compound 4 could be toxic to human normal cells while manzamine A is non-cytotoxic.

Several groups have been pushing the boundaries of existing MoIN applications to expand their utility for natural product de-replication. Notable efforts in this arena have been led by the lab of Jason Crawford, who has employed MoIN and bioinformatics-guided isotopic labeling to characterize elusive structural characteristics of the unstable and genotoxic *E. coli*-derived colibactin class that plays a role in colorectal cancer pathogenesis. However, despite its potential utility, only a small number of studies have exploited MoIN as a tool to expedite the discovery and evaluation of new drug-like small molecule natural products. Our networking results also support MoIN as a valuable workflow component for the discovery of new manzamine lead molecules. MS-based MoIN analysis facilitated the identification of putative manzamine A (1)-related structures that would have been challenging to identify using only MS information. Interestingly, two of these compounds contain modifications at the β-carboline moiety, a chemical group which has previously been shown to be important to 1 bioactivity and mechanism of action. Manzamine A (1) cytotoxicity has been linked to β-carboline mediated DNA intercalation in the major groove, contributing to cell cycle arrest. While this group is known to stabilize associations with GSK 3β-binding, a similar binding mode may be approximated with alternative heterocycles, which retain desirable, selective kinase inhibiting effects in the absence of DNA associations. Because of the differing routes of action of the Q-carboline and ring systems, replacement of the β-carboline may offer a promising strategy for the development of a better lead molecule with activity against cancer cells.

Figure 3A:
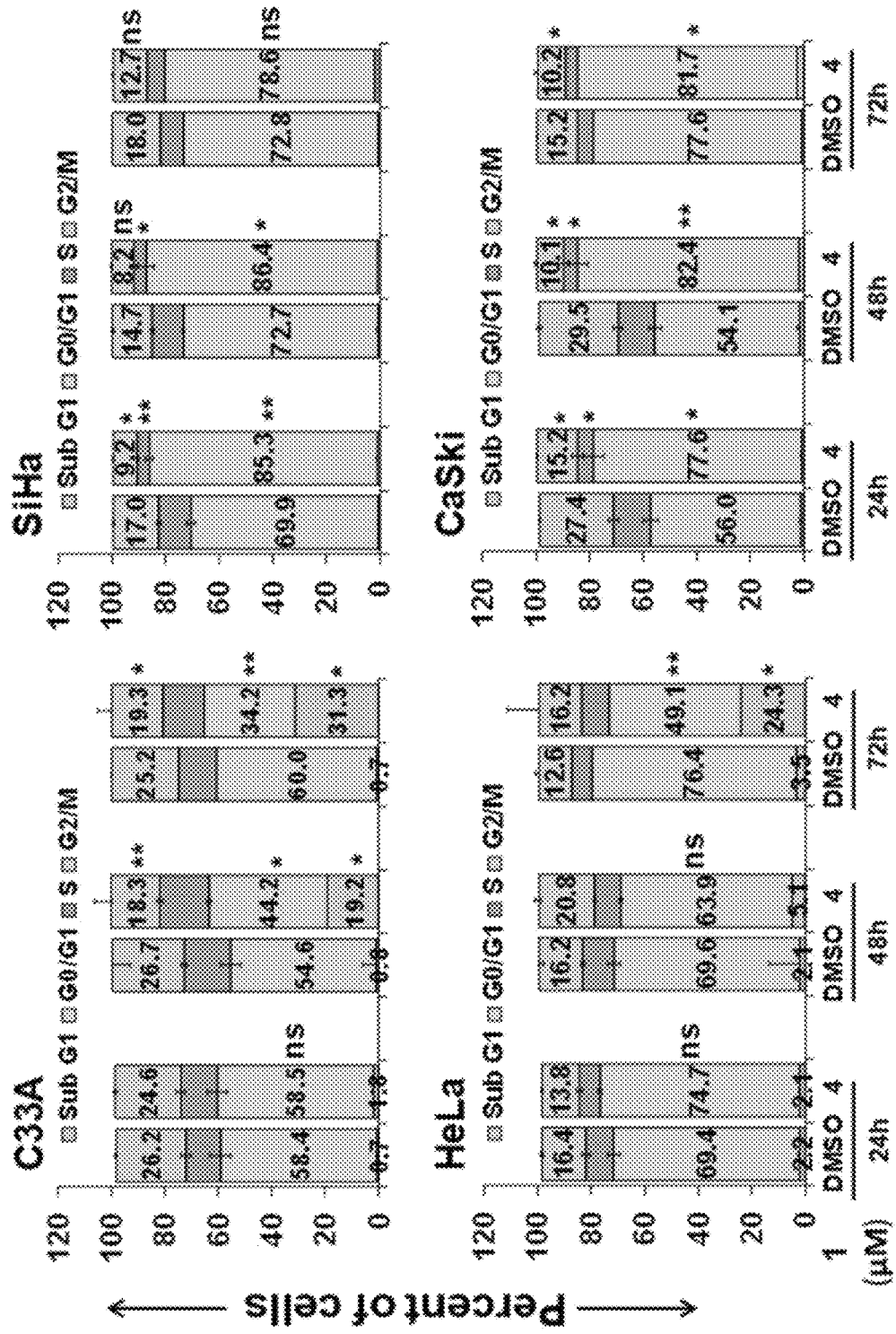
FIG. 3A shows a representation of manzamine A effects on cervical cancer cells treated with 4 µM concentration cell cycle regulation at three different time points.
Figure 3B:
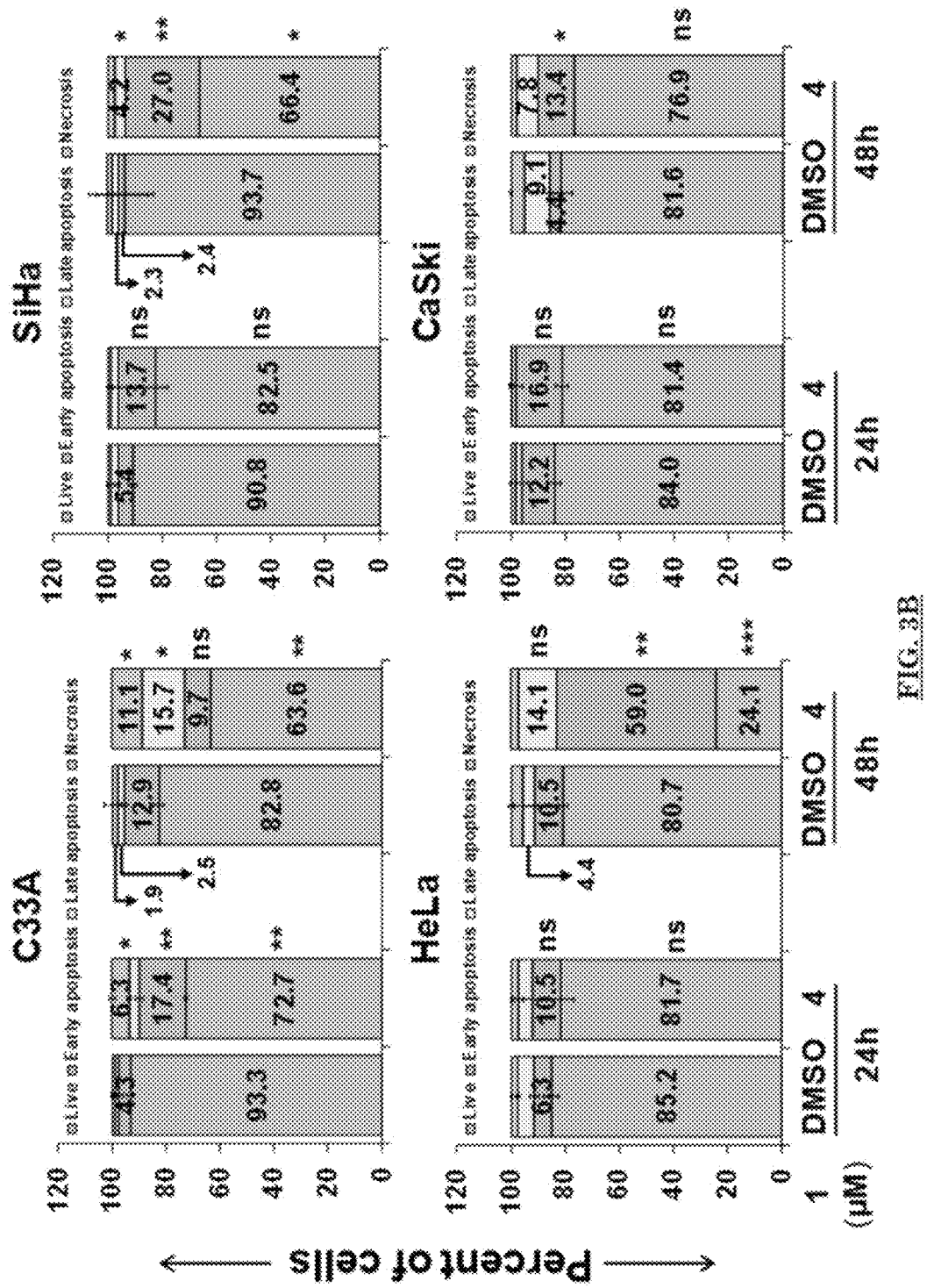
FIG. 3B shows apoptosis at 24 and 48 hours.

Differential Activation of G1 Phase Arrest and Apoptosis by Manzamine A (1). To understand the mechanism of manzamine A (1)-mediated cell growth inhibition, we analyzed the cell cycle distribution by flow cytometry in C33A, HeLa, SiHa, and CaSki cell lines. At 24 hours of treatment, C33A and HeLa cells showed minimal differences in the cell cycle distribution. However, there was a significant decrease in cell population in G0/G1 at 48 (p=0.043) and 72 (p=0.0012) hours with a corresponding increase in sub G1 cell population as compared to DMSO control, see FIG. 3A. FIGS. 3A and 3B show a representation of manzamine A (1) effect on cervical cancer cells treated with 4 μM concentration. FIG. 3A shows cell cycle regulation at 3 different time points: cells were stained with propidium iodide, and analyzed by flow cytometry to estimate the amount of cells in each phase of the cell cycle. FIG. 3B shows apoptosis at 24 and 48 hours: cells were stained with Annexin-FITC and PI, and analyzed by flow cytometry to estimate the amount of apoptosis and necrotic cell population. The values represent standard error from the mean (mean±SE). DMSO serves as control. The significance level represents; *p<0.05; p<0.001; *p<0001; and ns=non-significant. C33A cells also showed a significant decrease in G2/M cell population at 48 (p=0.005) and 72 hours (p=0.02) as compared to HeLa cells. On the contrary, compound manzamine A induces a significant increase in cell population at G0/G1-phase with a simultaneous decrease in S- and G2/M-phase in SiHa and CaSki cells, see FIG. 3A. Particularly at 4 µM concentration, the percentage of G0/G1 cell population in SiHa and CaSki increased to 1.2 fold (p=0.001) and 1.4 fold (p=0.011) at 24 hours, and 1.2 fold (p=0.03) and 1.5 fold (p=0.006) at 48 hours as compared to respective DMSO control.

Since programmed cell death (apoptosis) is a key mechanism by which anti-cancer drugs kill cancer cells, we determined the apoptotic effect of manzamine A on cervical cancer cells using annexin V and PI staining. Forty-eight hours treatment with compound manzamine A triggered significant increase in apoptosis in HeLa cells (p=0.005) as compared to C33A, SiHa, and CaSki cells, see FIG. 3B. However, C33A cells appear to be sensitive as manzamine A induces apoptosis (p=0.002) and necrosis (p=0.03) at 24 hours with a further increase in late apoptosis (p=0.03) and necrosis (p=0.04) at 48 hours. Given the sensitivity of C33A and HeLa cell lines to manzamine A, an increase in apoptosis was expected. Overall, the percentage of induced apoptotic cells (apoptosis+ necrosis) at 4 µM was higher at 48 hours as compared to respective DMSO control in C33A (36.5 vs 17.3), HeLa (75.9 vs 19.3), SiHa (33.6 vs 6.4), and CaSki (23.2 vs 18.4), suggesting the role of manzamine A inducing apoptosis in cervical cancer cells. CaSki cells were the least sensitive and corresponds to the $IC_{50}$ values as in FIG. 2.

Figure 4:
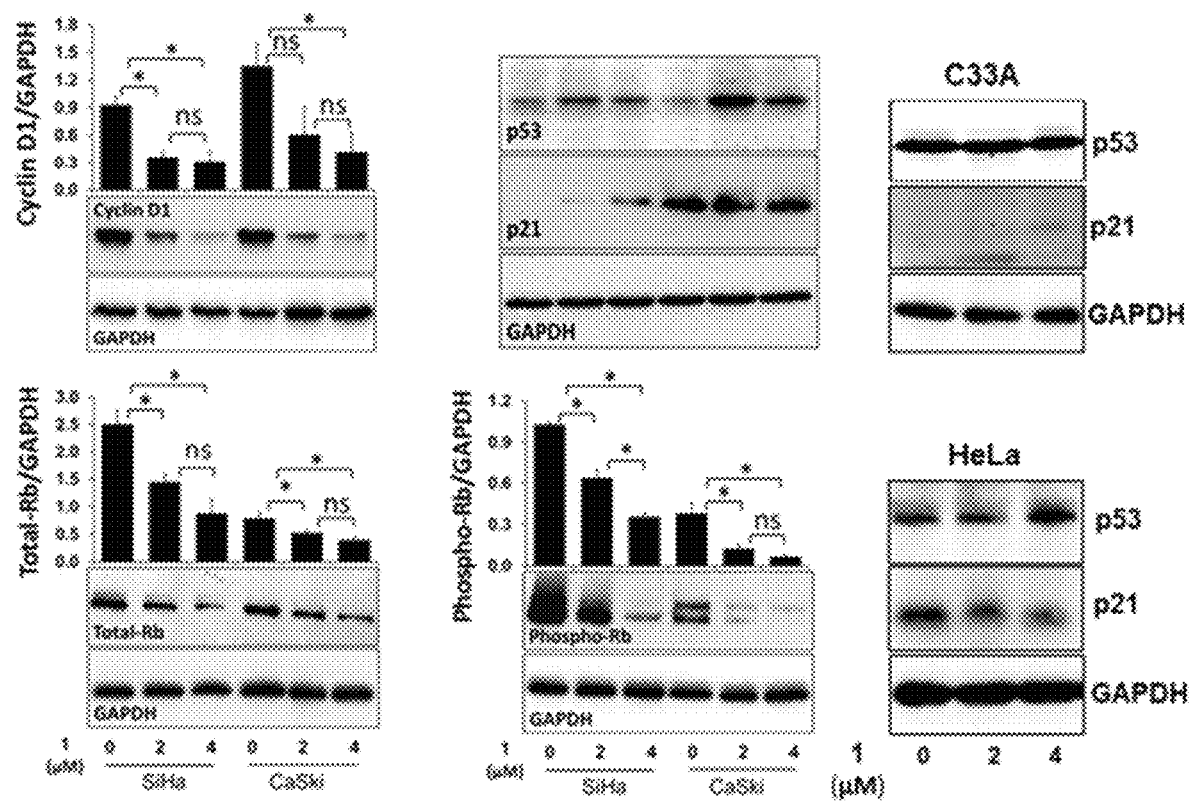
FIG. 4 shows the effect of manzamine A on the cell cycle regulatory proteins in human cervical cancer cell lines.

Molecular Targets of Manzamine A (1). HeLa, SiHa and CaSki cell lines represent the most common form of cervical cancer infected by the HPV type 16 (SiHa and CaSki) and 18 (HeLa). Cervical cancer is primarily aggravated by the sustained expression of HPV-derived E6 and E7 oncogenes utilizing distinct mechanisms that affect cell-cycle checkpoints. For instance, E6 promotes p53 degradation, while E7 is associated with phosphorylation of retinoblastoma (Rb) proteins. See (22) Huh, K.; Zhou, X.; Hayakawa, H.; Cho, J. Y.; Libermann, T. A.; Jin, J.; Harper, J. W.; Munger, K. *J. Virol.* 2007, 81, 9737-9747 and Talis, A. L.; Huibregtse, J. M.; Howley, P. M. *J. Biol. Chem.* 1998, 273, 6439-6445. Both p53 and Rb are tumor suppressor genes and play a critical role in maintaining cell cycle regulation. Additionally, interaction of cyclin D1 with Rb protein and their expression levels correlate positively in association with tumorigenesis. Therefore, we sought to examine the molecular targets of manzamine A leading to anti-cancer activity in cervical cancer. Following treatment with the natural sponge product manzamine A, we observed an increase in p53 and p21 protein level, and inhibition of cyclin D1, total Rb, and phospho-Rb, see FIG. 4, in SiHa and CaSki cells indicating that manzamine A may affect the regulation of both E6 and E7 oncogenes facilitating anti-cancer activities. FIG. 4 shows the effect of manzamine A (1) on the cell cycle regulatory proteins in human cervical cancer cell lines. Following the overnight attachment of $1\times10^6$ cells/well, the cells were treated with manzamine A (1) at 2 and 4 µM concentrations and incubated for 48 h. Cell lysates were prepared for protein analysis. HeLa cells showed a marginal increase in p53 level while p21 remains unchanged. On the contrary, HPV-negative C33A cells did not show any change in p53 protein level while p21 protein level was not-detectable following manzamine A treatment. These data indicate a difference in mechanism of manzamine A in HPV-positive and HPV-negative cell lines. However, detailed mechanistic studies of manzamine A determining anti-cancer effect are required to further substantiate these observations.

Figure 5:
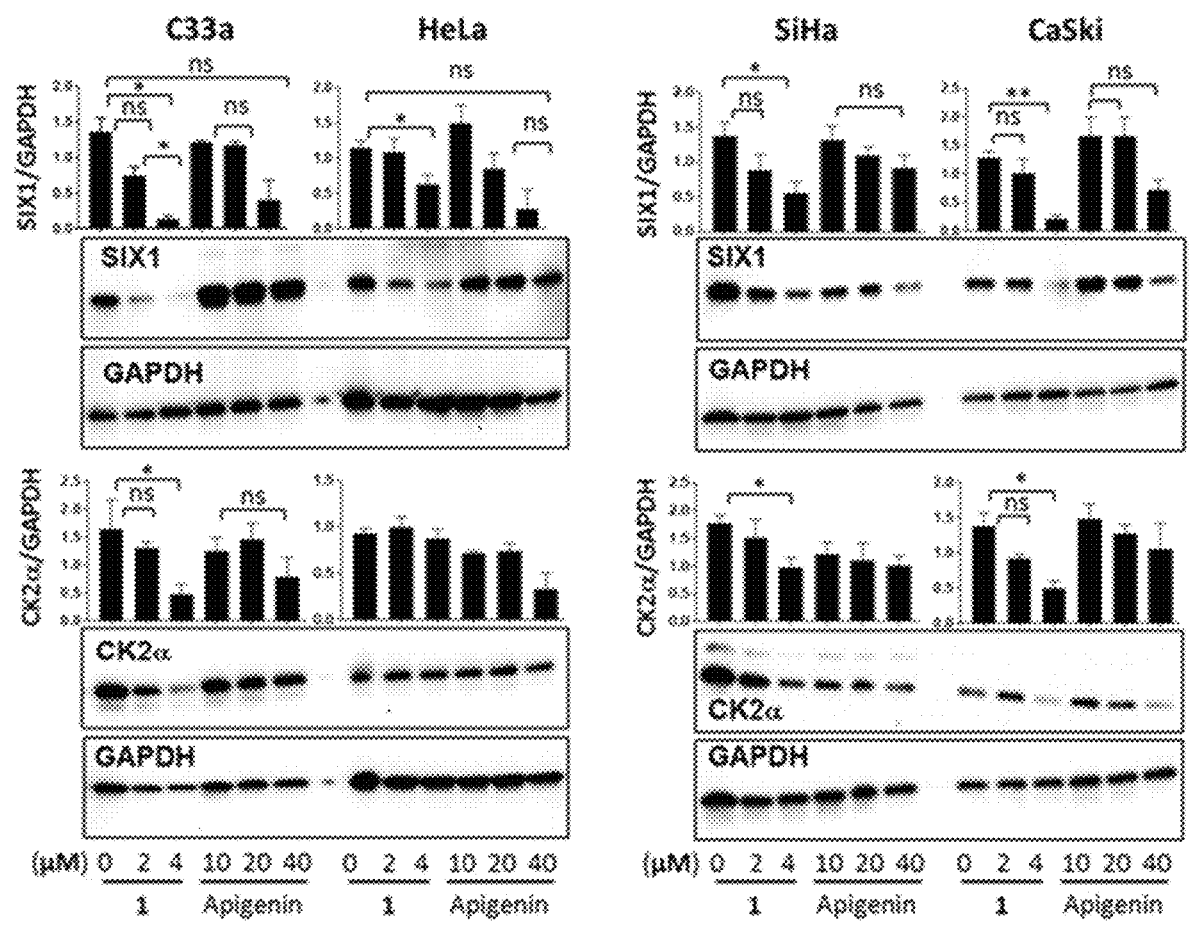
FIG. 5 shows an analysis of the effect of manzamine A and apigenin (a known inhibitor of CK2α protein) on a homeodomain containing transcription factor SIX1 and CK2α in human cervical cancer cell lines.

Anti-cancer activity of sponge product manzamine A was further evident from the inhibition of SIX1 protein, which is a homeodomain-containing transcription factor expressed at high levels in a variety of cancers, including cervical, colon, prostate, and breast cancers. See Xu, H. W.; Pirisi, L.; Creek, K. E. Virology 2015, 474, 144-153, Wan, F.; Miao, X.; Quraishi, I.; Kennedy, V.; Creek, K. E.; Pirisi, L. *Intl. J. Cancer.* 2008, 123, 32-40, Reichenberger, K. J.; Coletta, R. D.; Schulte, A. P.; Varella-Garcia, M.; Ford, H. L. *Cancer Res.* 2005, 65, 2668-2675, and Coletta, R. D.; Christensen, K.; Reichenberger, K. J.; Lamb, J.; Micomonaco, D.; Huang, L.; Wolf, D. M.; Muller-Tidow, C.; Golub, T. R.; Kawakami, K.; Ford, H. L. *Proc. Nl. Acad. Sci. U.S.A.* 2004, 101, 6478-6483. Overexpression of SIX1 leads to decreased expression of p53 as well as aggressive clinical behavior of cancers and poor outcomes. See, Reichenberger, K. J.; Coletta, R. D.; Schulte, A. P.; Varella-Garcia, M.; Ford, H. L. *Cancer Res.* 2005, 65, 2668-2675, Coletta, R. D.; Christensen, K.; Reichenberger, K. J.; Lamb, J.; Micomonaco, D.; Huang, L.; Wolf, D. M.; Muller-Tidow, C.; Golub, T. R.; Kawakami, K.; Ford, H. L. *Proc. Nl. Acad. Sci. U.S.A* 2004, 101, 6478-6483, Towers, C. G.; Guarnieri, A. L.; Micalizzi, D. S.; Harrell, J. C.; Gillen, A. E.; Kim, J.; Wang, C. A.; Oliphant, M. U.; Drasin, D. J.; Guney, M. A.; Kabos, P.; Sartorius, C. A.; Tan, A. C.; Perou, C. M.; Espinosa, J. M.; Ford, H. L. *Nat. Commun.* 2015, 6, 10077. Interestingly, the E7 oncogene induces SIX1 expression in cervical intraepithelial neoplasia and cervical cancer cells, and accumulation of cyclin D1 in tumor cells resulting in tumorigenesis. See Liu, D.; Zhang, X. X.; Xi, B. X.; Wan, D. Y.; Li, L.; Zhou, J.; Wang, W.; Ma, D.; Wang, H.; Gao, Q. L. *Int. J. Oncol.* 2014, 45, 1232-1240 and Yu, Y.; Davicioni, E.; Triche, T. J.; Merlino, G. Cancer Res. 2006, 66, 1982-1989. The current disclosure demonstrates that manzamine A significantly inhibits the SIX1 protein both in HPV-negative C33A cells and HPV-positive HeLa, SiHa, and CaSki cells, see FIG. 5. FIG. 5 shows analysis of the effect of manzamine A (1) and apigenin (a known inhibitor of CK2α protein) on a homeodomain containing transcription factor SIX1 and CK2α in human cervical cancer cell lines. Following the overnight attachment of $1\times10^6$ cells/well, the cells were treated with manzamine A (1) at 2 and 4 µM or apigenin at 10, 20, and 40 µM concentrations, and incubated for 48 h. Cell lysates were prepared for protein analysis. These observations suggest that manzamine A induced cytotoxicity in cervical cancer cells across this dose range is not solely mediated by perturbing the E6/7 axis. Another possible mechanism of manzamine A action is linked with the inhibition of glycogen synthase kinase (GSK)-3β, a biological effect that is supported by structural activity studies. See Hamann, M.; Alonso, D.; Martin-Aparicio, E.; Fuertes, A.; Perez-Puerto, M. J.; Castro, A.; Morales, S.; Navarro, M. L.; Del Monte-Millan, M.; Medina, M.; Pennaka, H.; Balaiah, A.; Peng, J.; Cook, J.; Wahyuono, S.; Martinez, A. *J. Nat. Prod.* 2007, 70, 1397-1405 and Yu, Y.; Davicioni, E.; Triche, T. J.; Merlino, G. *Cancer Res.* 2006, 66, 1982-1989. Recent study in colorectal cancer showed that compound manzamine A induced cell cycle arrest in G0/G1 via inhibition of cyclin-dependent kinases and caspase-dependent apoptotic cell death. Lin, L. C.; Kuo, T. T.; Chang, H. Y.; Liu, W. S.; Hsia, S. M.; Huang, T. C. *Mar. Drugs* 2018, 16. Furthermore, in pancreatic cancer studies manzamine A has been shown to sensitize pancreatic adenocarcinoma cells towards TRAIL-induced apoptosis, decreasing cell dissociation and migration by inhibiting autophagy through prevention of autophagosome turnover. See, Kallifatidis, G.; Hoepfner, D.; Jaeg, T.; Guzman, E. A.; Wright, A. E. Mar. Drugs 2013, 11, 3500-3516 and Ford, H. L.; Landesman-Bollag, E.; Dacwag, C. S.; Stukenberg, P. T.; Pardee, A. B.; Seldin, D. C. J. Biol. Chem. 2000, 275, 22245-22254. It is not currently clear, however, whether manzamine A affects GSK3β and TNF-dependent pathways in cervical cancer. While the differences in mechanism of manzamine A action could be due to differential regulatory pathways in different cancer types, we continued our efforts to determine the mechanism of anticancer activity in cervical cancer.

Figure 6:
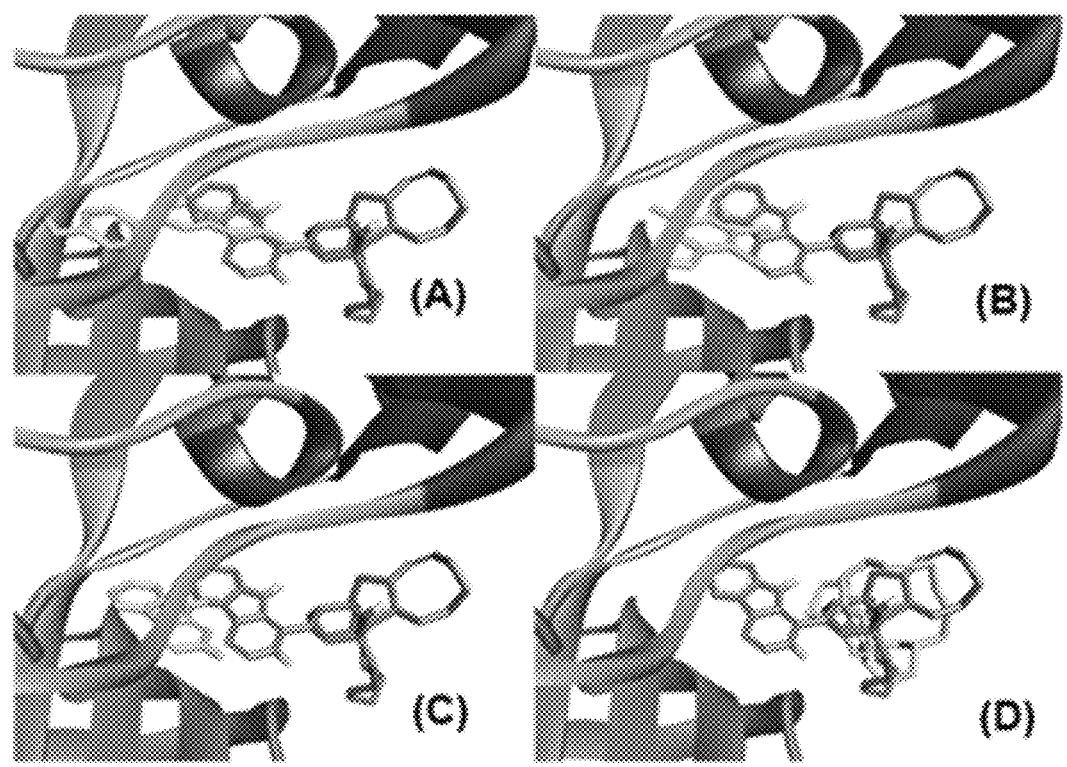
FIG. 6 shows a comparison of CK2α binding space for manzamine A vs. TBB (A), apigenin (B), β-carboline (C), and ircinal A (D).
Figure 7:
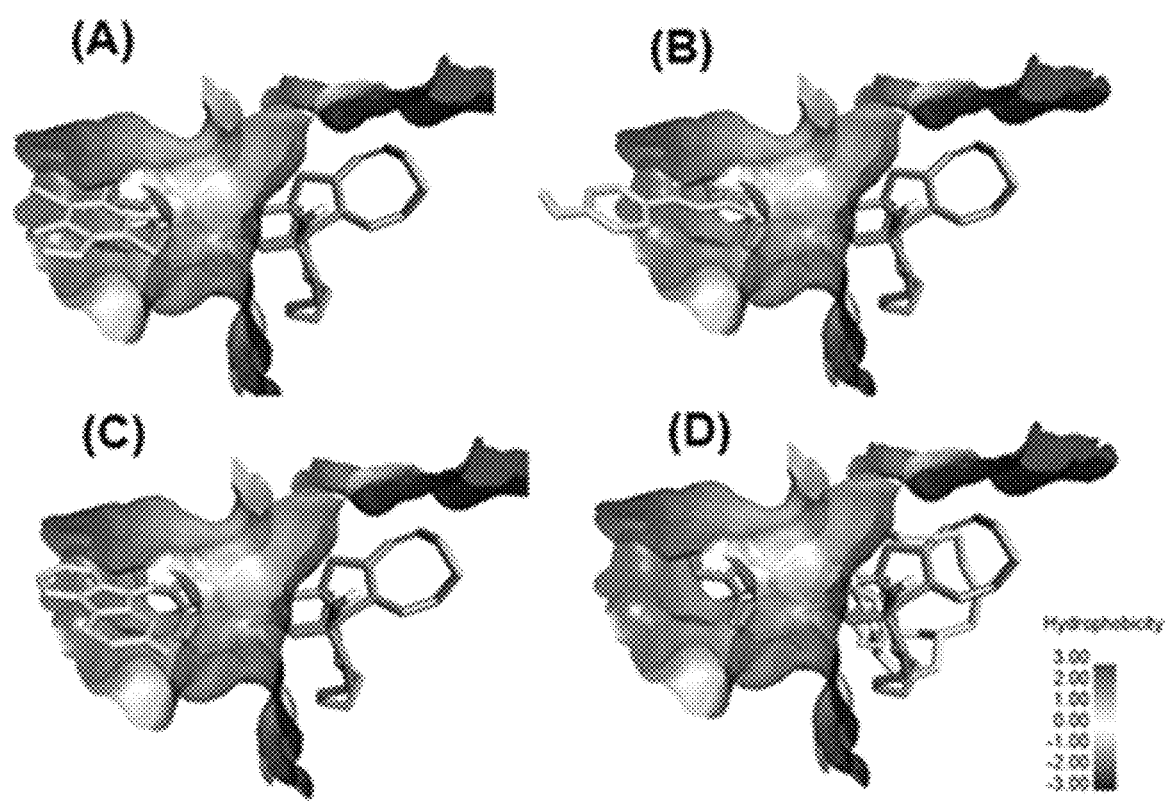
FIG. 7 shows a comparison of CK2α binding interactions for manzamine A (1) vs. TBB (A), apigenin (B), β-carboline (C), and ircinal A (D).

Molecular Docking of Manzamine A (1). Molecular docking assay is an effective tool to carry out a preliminary evaluation of possible bioactivity. Previous studies have indicated that in addition to E7 oncogene, SIX1 expression is regulated by protein kinase CK2. See, Liu, D.; Zhang, X. X.; Xi, B. X.; Wan, D. Y.; Li, L.; Zhou, J.; Wang, W.; Ma, D.; Wang, H.; Gao, Q. L. Int. J. Oncol. 2014, 45, 1232-1240 and Ford, H. L.; Landesman-Bollag, E.; Dacwag, C. S.; Stukenberg, P. T.; Pardee, A. B.; Seldin, D. C. J. Biol. Chem. 2000, 275, 22245-22254. SIX1 contains conserved CK2 sites at position Thr-490, Ile-491, Trp-492 and Asp-493. Inhibition of CK2 results in the diminished phosphorylation of SIX1 and leads to a dose-dependent arrest at the G2/M boundary, suggesting SIX1 as a plausible target of CK2. Molecular docking study of manzamine A was performed on CK2 kinase alpha subunit (CK2a) protein to evaluate the ligand-protein interactions and binding affinity, see FIG. 6. FIG. 6 shows Comparison of CK2α binding space for manzamine A (1) vs. TBB (A), apigenin (B), β-carboline (C), and ircinal A (D). Manzamine A (1) structure is in gray color, while the yellow structures represent known inhibitors. The binding affinity and interactions of manzamine A (1) to CK2α was compared to that of β-carboline, ircinal A (5), 4,5,6,7-tetrabromobenzimidazole (TBB) and apigenin. TBB and apigenin are inhibitors of CK2a, while β-carboline and ircinal A (5) represent the partial structures of manzamine A (1). The results showed manzamine A has a better binding affinity (−8.1 KCal/mol) than the known CK2α inhibitor TBB (−7.4 KCal/mol). Both apigenin (−9.1 KCal/mol) and β-carboline (−8.6 KCal/mol) displayed better binding affinity than manzamine A while 5 (−5.1 KCal/mol) showed the most unfavorable binding affinity. The comparison of binding space and interactions between manzamine A (1) with TBB, apigenin, β-carboline and ircinal A (5) are shown in FIGS. 6 and 7. FIG. 7 shows a comparison of CK2α binding interactions for manzamine A (1) vs. TBB (A), apigenin (B), β-carboline (C), and ircinal A (D). Manzamine A (1) structure is in gray color, while the yellow structures represent known inhibitors. The results indicated that manzamine A shared similar binding interactions and space with the known CK2α inhibitors, i.e., TBB and apigenin. The displayed favorable binding of 1 to CK2α is due to the strong hydrophobic interactions in the binding pocket, see FIG. 7. In support of our in-silico docking model, we examined the effect of manzamine A (1) on CK2α protein correspond to apigenin effect on SIX1 protein level. We demonstrated that compound manzamine A decreased the level of CK2α protein corresponds to SIX1 in C33A, SiHa, and CaSki cells, see FIG. 5. Apigenin also decreased the proteins level of SIX1 and CK2a, however at a much higher concertation (40 μM). These data suggest that manzamine A (1) is almost 10-times more potent in inhibiting CK2α and SIX1 target proteins as compared to the known inhibitor apigenin. Despite sensitivity of HeLa cells to manzamine A, we did not observe CK2α inhibition indicating an additional signaling mechanism of cancer cell killing. The current disclosure shows that β-carboline moiety of manzamine A is able to extend deep into the binding pocket to form hydrophobic interactions with similar amino acid residues (Met-163, Val-116, Ile-66, Val-53, Val-45) as TBB and apigenin, while the ircinal moiety of manzamine A is located at the entrance of binding pocket. Docking studies on β-carboline and ircinal A (5) are in agreement with manzamine A docking results, showing strong binding of β-carboline at the binding pocket while 5 exhibits poor binding at the entrance of the binding pocket. These observations added another potential application of manzamine A as CK2α-inhibitor and present a new avenue of study for manzamine A (1).

The manzamine class of marine alkaloids is attractive in its potential for the development of novel therapeutics. This group has among the most extensively studied marine natural products to date, being found in more than 16 species of Indo-Pacific sponges distributed within distinct geographical regions. The first of this class, manzamine A (1), from *Haliclona* has demonstrated unprecedented potency against drug-resistant forms of the malaria parasite (*Plasmodium* spp.), showing greater potency and efficacy as compared to a number of FDA-approved antimalarial drugs, including chloroquine. These molecules also show interesting activity as neuroprotective and anti-inflammatory agents, HIV/AIDS-associated opportunistic infections, and inhibition of cancer proliferative and metastatic activity. See Ridley, R. G.; Matile, H.; Jaquet, C.; Dorn, A.; Hofheinz, W.; Leupin, W.; Masciadri, R.; Theil, F. P.; Richter, W. F.; Girometta, M. A.; Guenzi, A.; Urwyler, H.; Gocke, E.; Potthast, J. M.; Csato, M.; Thomas, A.; Peters, W. *Antimicrob. Agents Chemother.* 1997, 41, 677-686. We showed that manzamine A (1) treatment leads to significant decrease in the level of SIX1 and CK2α proteins along with the regulation of cell cycle related checkpoint proteins in cervical cancer cell lines suggesting that manzamine A might be active in vivo against cancers that express high levels of SIX1. In a direct comparison to apigenin, an inhibitor of CK2a, this study demonstrated that manzamine A is about ten-times more potent in inhibiting CK2α and SIX1 proteins than apigenin. We have determined the oral toxicity profile of manzamine A in a healthy rodent (rat) model (unpublished) with an $LD_{50}$ between 200 and 300 mg/kg body weight, comparable to that of acetaminophen (338 mg/kg orally) in mice. While observed weight loss at high doses resulted in termination of manzamine A for drug development by the Medicines for Malaria Venture, whose primary target patient group is very young children. It is anticipated that short-term weight-loss would be less problematic or would not necessarily offset the therapeutic gain in cancer patients.

While advantageous for natural product de-replication in its current form, the MolN platform may benefit from the addition of applications which marry existing networking capabilities with utilities for molecular formula prediction and structural analysis, taking advantage of advanced algorithms which simultaneously analyze human resources management system (HRMS) and MS information contained within the data output. Given that current workflows require data transfer and parallel analysis within multiple software applications, an integrated platform such as this would represent a powerful tool for streamlined and efficient prioritization and deconvolution of molecular features with drug-like properties. Given the natural diversity of manzamine compounds, it is possible that many more manzamine structures remain to be characterized within this rich reservoir of sponge secondary metabolites in addition to the potential to generate more useful molecules using rational drug design.

EXPERIMENTAL SECTION

Cell Culture. Human cervical cancer cell lines C33A, HeLa, SiHa, and CaSki were purchased from the American Type Culture Collection (ATCC, Manassas, VA). Cells were grown in Dulbecco's Modified Eagle Medium (DMEM) medium supplemented with 10% fetal bovine serum, 2 mM L-glutamine, 100 U/ml of penicillin-streptomycin, and maintained at 37° C. with 5% $CO_2$ in a humidified incubator.

Generation of Normal Human Keratinocytes (HKc). The generation and processing of normal HKc from de-identified foreskin tissue samples has previously been described in our studies, see Pirisi, L.; Yasumoto, S.; Feller, M.; Doniger, J.; DiPaolo, J. A. *J. Virol.* 1987, 61, 1061-1066, and was implemented with the following modifications: dispase was used in lieu of collagenase, and a trypsinization step was added to release the epidermal cells. Briefly, to generate normal HKc primary cultures, the foreskin tissue, free of subcutaneous tissue, was placed in 10% dispase in phosphate buffer saline (PBS) and incubated overnight at 37° C. The next day, the epidermis was separated from the dermis, and processed mechanically by shredding the tissue into smaller pieces that were then treated with Trypsin/EDTA for 10 minutes at 37° C. Following the addition of fetal bovine serum (10%) to stop the trypsin action, cells were collected by centrifugation and plated in keratinocytes serum free medium (KSFM).

Extraction and Isolation of Manzamine A (1). Lipophilic alkaloid extracts were previously prepared from the Indonesian sponge *Acanthostrongylophora* (collected from Manado Bay, Northern Sulawesi, Indonesia in 2003). Crude material was separated using vacuum liquid chromatography and manzamine A purified by crystallization. Purified manzamine A was then transformed into its hydrochloride salt and recrystallized to reach high purity (>99%) and optimized aqueous solubility as described previously. See Yousaf, M.; Hammond, N. L.; Peng, J.; Wahyuono, S.; McIntosh, K. A.; Charman, W. N.; Mayer, A. M.; Hamann, M. T. *J. Med. Chem.* 2004, 47, 3512-3517 and Rao, K. V.; Donia, M. S.; Peng, J.; Garcia-Palomero, E.; Alonso, D.; Martinez, A.; Medina, M.; Franzblau, S. G.; Tekwani, B. L.; Khan, S. I.; Wahyuono, S.; Willett, K. L.; Hamann, M. T. *J. Nat. Prod.* 2006, 69, 1034-1040.

Cell Viability Assay. Cell viability was measured by using Cell Titer-Glo Luminescent Cell Viability Assay Kit (Promega, Leiden, Netherlands) according to the manufacturer's instructions. Briefly, $2 \times 10^4$ cells were seeded in 96 well plates. Next day, cells were treated with different concentrations of MA (0-40 µM) for 24, 48 and 72 hours. Percent viability was calculated using the formula: percent (%) viability=100×(Treatment/Control). The $IC_{50}$ value was calculated from the dose responsive sigmoid curve generated from % viability using GrpaphPad Prism 7 software.

Cell Growth Kinetics. Cervical cancer cells ($1 \times 10^6$) or HKc ($2 \times 10^5$) were plated in 100 mm tissue culture petri dish or 6-well plates. Following overnight incubation, cells were treated with 2 µM or 4 µM concentrations of manzamine A (1) derivatives for different time points (24, 48 and 72 hours). Dimethyl sulphoxide (DMSO) was used as control. The cell proliferation activity was determined by cell counting under the microscope with a hemocytometer using trypan blue staining.

Colony Formation Assay. Cancer cell lines were seeded at a density of $1 \times 10^3$ cells/ml in 6-well plates. Following overnight incubation, the cells were treated with manzamine A (1) (2 µM and 4 µM) and incubated in a tissue culture incubator at 37° C. with 5% $CO_2$. After one week, the developed cell colonies were fixed with 4% paraformaldehyde, stained with 0.5% crystal violet, and were photographed.

Cell-cycle and Apoptosis Analysis. Cervical cancer cells were seeded and treated with different concentrations of manzamine A (1) as above. Following trypsinization, one part of the cells was washed with PBS and fixed in chilled 70% ethanol on ice for 30 min. Cells were treated with RNAse A (1 mg/ml) at room temperature for 30 min and stained with propidium iodide (PI: 20 µg/ml). Cell-cycle distribution was analyzed by flow cytometry (Beckman Coulter Epics Elite, Beckman). A minimum of 10,000 events were counted per sample, and the data were analyzed using CXP software (Beckman Coulter) for the proportions of cells in G0/G1, S and G2/M phases of the cell cycle. The second part of the cells were washed twice with PBS and re-suspended in the buffer containing Alexa Fluor conjugated-Annexin-V and PI (Life Technologies, USA). The double staining of the cells was analyzed by flow cytometric analysis. A total of 10,000 cell events were collected to analyze the extent of early, late apoptosis, or necrosis from each sample with the percentages of bound annexin-$V^+/PI^-$, annexin $V^+/PI^+$, and annexin $V^-/PI^+$, respectively.

Protein Expression Analysis. C33A, HeLa, SiHa and CaSki cells were seeded at a density of $1 \times 10^6$ cells/100 mm petri dish. The next day, the cells were treated with 2 µM or 4 µM concentrations of manzamine A (1) or with 10, 20, or 40 µM concentrations with apigenin (Sigma, MO) and incubated for 48 hours. At the given time-point, the cells were harvested by trypsinization, washed with PBS, and lysed using radioimmunoprecipitation assay (RIPA) buffer containing a cocktail of protease inhibitors (Sigma, MO) to extract protein. Following quantification by colorimetric assay (Bio-Rad), equal amount of protein was loaded on to SDS-polyacrylamide gel and transferred to polyvinylidene difluoride (PVDF) membrane, which was blocked in 5% non-fat dry milk in tris-buffered saline with tween-20 (TBST) and incubated with primary antibody against p53, p21, Cyclin D1, SIX1, GAPDH (Cell signaling) or CK2α (R&D Systems) at a 1:500 dilution. For total CK2a, Rb and pRb, the blocking and antibody dilutions were made in 3% bovine serum albumin (BSA). The membrane was washed with TBST and incubated with secondary IgG HRP conjugate at 1:2000 dilution. The specific band of the protein was visualized with chemiluminescent reagent exposed onto BioMax Film (Kodak) and ChemoDoc-$it^2$ imager (UVP).

Molecular Networking. Alkaloid samples were resolubilized in 100% methanol and analyzed on an online LC-ESI-MSMS system comprised of an Agilent 1100 series pump/autosampler/diode array coupled to a Bruker Impact II QqTOF. Samples (500 ng) were separated on a TMS-endcapped C18 RPLC column (Kinetex® 5 µM 100 Å, 250×4.6 mm column) with a gradient of 10-90% acetonitrile+0.1% formic acid over 30 min (1 mL/min). Spectra were acquired within the 150-2000 m/z mass range, and the top 3 signals (300-1700 m/z) selected for $MS^2$ fragmentation by collision induced dissociation within a 2.0 Da window (50 eV), allowing for dynamic exclusion after 3 observations (30 s). Raw data were uploaded to the open-source Spectral Networking script at http://gnps.ucsd/edu, and filtered for features $\geq 2.5^3$ counts. Spectra were merged employing parent mass and MS/MS fragment ion tolerance threshold of 0.1 Da. Only features with a minimum of 5 observations were retained in the network. Edges were filtered for cosine scores above 0.60, retaining nodes which appeared in each other's respective top 10 most similar nodes. See Watrous, J.; Roach, P.; Alexandrov, T.; Heath, B.

S.; Yang, J. Y.; Kersten, R. D.; van der Voort, M.; Pogliano, K.; Gross, H.; Raaijmakers, J. M.; Moore, B. S.; Laskin, J.; Bandeira, N.; Dorrestein, P. C. Proc. *Natl. Acad. Sci. U.S.A* 2012, 109, E1743-1752 and Winnikoff, J. R.; Glukhov, E.; Watrous, J.; Dorrestein, P. C.; Gerwick, W. H. *J. Antibiot.* 2014, 67, 105-112. The resulting network was visualized in Cytoscape 3.4.0. See, Balkovec, J. M.; Hughes, D. L.; Masurekar, P. S.; Sable, C. A.; Schwartz, R. E.; Singh, S. B. *Nat. Prod. Rep.* 2014, 31, 15-34.

Nuclear Magnetic Resonance (NMR). 1H and 13C NMR spectra were recorded on a Bruker Nanobay 400 MHz (9.4 T) spectrometer in pyridine-D5. Chemical shifts are expressed in parts per million and were referenced to residual solvent peaks ($\delta$H 7.22, 7.58, and 8.74; $\delta$C 123.9, 135.9, 150.4). Preparation scale HPLC separation was performed using Waters 4000 Delta Prep system.

Molecular Docking. The MM2 energy-minimized 3D structure of ligands, i.e., MA, $\beta$-carboline, ircinal A (5), 4,5,6,7-tetrabromobenzimidazole (TBB) and apigenin were optimized using ChemBio3D Ultra version 12.0. The crystal structure of *Zea mays* CK2 kinase alpha subunit (CK2$\alpha$) (PDB ID: 1J91) receptor protein was obtained from Protein Data Bank (www.rcsb.org). See, Battistutta, R.; De Moliner, E.; Sarno, S.; Zanotti, G.; Pinna, L. A. Protein Sci. 2001, 10, 2200-2206. The ligands and receptor for molecular docking experiments were prepared using AutoDockTools version 1.5.6, in which the polar hydrogens were added to these structures. See, Sanner, M. F. *J. Mol. Graph Model* 1999, 17, 57-61 and Trott, O.; Olson, A. J. *J. Comput. Chem.* 2010, 31, 455-461. The grit box parameter was set to cover the binding pocket in the receptor, with x-dimension=20; y-dimension=20; z-dimension=20; X-center=21.774; Y-center=8.022; and Z-center=19.144. The grit box spacing was set as 1.0 Å. The docking was performed using AutoDock Vina and the binding affinity were measured. The outputs were visualized and analyzed using BIOVIA Discovery Studio Visualizer version 17.2.0.

Statistical Analysis. All experiments were performed in duplicates and repeated 3 to 4 times with similar results. All values are expressed as mean±standard error of the mean (SEM). Statistical analysis was performed using GraphPad Prism software (GraphPad Software, Inc., CA). The value of $p<0.05$ was considered statistically significant.

Sequence Listing Free Text

The Homeobox protein SIX1 sequence listing, from *Homo sapiens*, with a sequence length of 284, is shown below:

<110> University of South Carolina
<120> Use of Manzamines as Antiproliferative Agent
<130> 2033101.0000154
<140> Unknown
<141> 2021 Feb. 6
<150> U.S. Provisional Application No. 62/970,750
<151> 2020 Feb. 6
<160> 1
<170> PatentIn
<210> 1
<211> 284
<212> PRTN
<213> *Homo sapiens*
<221> CDS
<222> 1 . . . 284
<400> 1

```
Met Ser Met Leu Pro Ser Phe Gly Phe Thr Gln Glu Gln Val Ala Cys
1               5                   10                  15

Val Cys Glu Val Leu Gln Gln Gly Gly Asn Leu Glu Arg Leu Gly Arg
                20                  25                  30

Phe Leu Trp Ser Leu Pro Ala Cys Asp His Leu His Lys Asn Glu Ser
                35                  40                  45

Val Leu Lys Ala Lys Ala Val Val Ala Phe His Arg Gly Asn Phe Arg
            50                  55                  60

Glu Leu Tyr Lys Ile Leu Glu Ser His Gln Phe Ser Pro His Asn His
65                  70                  75                  80

Pro Lys Leu Gln Gln Leu Trp Leu Lys Ala His Tyr Val Glu Ala Glu
                85                  90                  95

Lys Leu Arg Gly Arg Pro Leu Gly Ala Val Gly Lys Tyr Arg Val Arg
                100                 105                 110

Arg Lys Phe Pro Leu Pro Arg Thr Ile Trp Asp Gly Glu Glu Thr Ser
            115                 120                 125

Tyr Cys Phe Lys Glu Lys Ser Arg Gly Val Leu Arg Glu Trp Tyr Ala
        130                 135                 140

His Asn Pro Tyr Pro Ser Pro Arg Glu Lys Arg Glu Leu Ala Glu Ala
145                 150                 155                 160

Thr Gly Leu Thr Thr Thr Gln Val Ser Asn Trp Phe Lys Asn Arg Arg
                165                 170                 175

Gln Arg Asp Arg Ala Ala Glu Ala Lys Glu Arg Glu Asn Thr Glu Asn
                180                 185                 190

Asn Asn Ser Ser Ser Asn Lys Gln Asn Gln Leu Ser Pro Leu Glu Gly
            195                 200                 205
```

Various modifications and variations of the described methods, pharmaceutical compositions, and kits of the disclosure will be apparent to those skilled in the art without departing from the scope and spirit of the disclosure. Although the disclosure has been described in connection with specific embodiments, it will be understood that it is capable of further modifications and that the disclosure as claimed should not be unduly limited to such specific embodiments. Indeed, various modifications of the described modes for carrying out the disclosure that are obvious to those skilled in the art are intended to be within the scope of the disclosure. This application is intended to cover any variations, uses, or adaptations of the disclosure following, in general, the principles of the disclosure and including such departures from the present disclosure come within known customary practice within the art to which the disclosure pertains and may be applied to the essential features herein before set forth.

SEQUENCE LISTING

```
<160> NUMBER OF SEQ ID NOS: 1

<210> SEQ ID NO 1
<211> LENGTH: 284
<212> TYPE: PRT
<213> ORGANISM: Homo sapiens

<400> SEQUENCE: 1

Met Ser Met Leu Pro Ser Phe Gly Phe Thr Gln Glu Gln Val Ala Cys
1               5                   10                  15

Val Cys Glu Val Leu Gln Gln Gly Gly Asn Leu Glu Arg Leu Gly Arg
                20                  25                  30

Phe Leu Trp Ser Leu Pro Ala Cys Asp His Leu His Lys Asn Glu Ser
            35                  40                  45

Val Leu Lys Ala Lys Ala Val Val Ala Phe His Arg Gly Asn Phe Arg
        50                  55                  60

Glu Leu Tyr Lys Ile Leu Glu Ser His Gln Phe Ser Pro His Asn His
65                  70                  75                  80

Pro Lys Leu Gln Gln Leu Trp Leu Lys Ala His Tyr Val Glu Ala Glu
                85                  90                  95

Lys Leu Arg Gly Arg Pro Leu Gly Ala Val Gly Lys Tyr Arg Val Arg
                100                 105                 110

Arg Lys Phe Pro Leu Pro Arg Thr Ile Trp Asp Gly Glu Glu Thr Ser
            115                 120                 125

Tyr Cys Phe Lys Glu Lys Ser Arg Gly Val Leu Arg Glu Trp Tyr Ala
        130                 135                 140

His Asn Pro Tyr Pro Ser Pro Arg Glu Lys Arg Glu Leu Ala Glu Ala
145                 150                 155                 160

Thr Gly Leu Thr Thr Thr Gln Val Ser Asn Trp Phe Lys Asn Arg Arg
                165                 170                 175

Gln Arg Asp Arg Ala Ala Glu Ala Lys Glu Arg Glu Asn Thr Glu Asn
                180                 185                 190

Asn Asn Ser Ser Ser Asn Lys Gln Asn Gln Leu Ser Pro Leu Glu Gly
            195                 200                 205

Gly Lys Pro Leu Met Ser Ser Ser Glu Glu Glu Phe Ser Pro Pro Gln
    210                 215                 220

Ser Pro Asp Gln Asn Ser Val Leu Leu Leu Gln Gly Asn Met Gly His
225                 230                 235                 240

Ala Arg Ser Ser Asn Tyr Ser Leu Pro Gly Leu Thr Ala Ser Gln Pro
                245                 250                 255

Ser His Gly Leu Gln Thr His Gln His Gln Leu Gln Asp Ser Leu Leu
            260                 265                 270

Gly Pro Leu Thr Ser Ser Leu Val Asp Leu Gly Ser
        275                 280
```

-continued

```
Gly Lys Pro Leu Met Ser Ser Ser Glu Glu Glu Phe Ser Pro Pro Gln
    210                 215             220
Ser Pro Asp Gln Asn Ser Val Leu Leu Leu Gln Gly Asn Met Gly His
225             230                 235                 240
Ala Arg Ser Ser Asn Tyr Ser Leu Pro Gly Leu Thr Ala Ser Gln Pro
                245             250                 255
Ser His Gly Leu Gln Thr His Gln His Gln Leu Gln Asp Ser Leu Leu
            260         265                 270
Gly Pro Leu Thr Ser Ser Leu Val Asp Leu Gly Ser
            275             280
```

What is claimed is:

1. A method for suppressing proliferation of cancer cells comprising:
   administering a therapeutically effective amount of Manzamine A or a salt thereof to a subject;
   wherein the Manzamine A or a salt thereof binds with Casein Kinase 2, which is involved with oncogenesis; and
   wherein the bound Manzamine A or a salt thereof and Casein Kinase 2 regulate oncoprotein SIX1 with a protein sequence of SEQ. 1, which is associated with cervical cancer.

2. The method of claim 1, wherein the Manzamine A or a salt thereof is noncytotoxic in concentrations up to 4 µM.

3. The method of claim 1, wherein the cancer includes, colon, pancreatic, prostrate, and breast cancer.

4. The method of claim 1, wherein the Manzamine A or a salt thereof is naturally occurring.

5. The method of claim 1, wherein administering the Manzamine A or a salt thereof restores expression of proteins inducing cell apoptosis.

6. The method of claim 1, wherein the at least one Manzamine A or a salt thereof is administered in a dose concentration ranging from 1 µM to 40 µM.

* * * * *